US012712067B2

(12) United States Patent
Fabricius

(10) Patent No.: US 12,712,067 B2
(45) Date of Patent: Aug. 18, 2026

(54) METHOD FOR DIGITAL IMAGE PROCESSING OF MEDICAL IMAGES RECORDED WITH A MEDICAL IMAGING DEVICE AND COMPLETE MEDICAL SYSTEM

(71) Applicant: Siemens Healthcare GmbH, Erlangen (DE)

(72) Inventor: Uwe Fabricius, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 326 days.

(21) Appl. No.: 18/524,956

(22) Filed: Nov. 30, 2023

(65) Prior Publication Data

US 2024/0203565 A1 Jun. 20, 2024

(30) Foreign Application Priority Data

Dec. 20, 2022 (EP) .................................... 22215016

(51) Int. Cl.

*G16H 30/40* (2018.01)
*G06T 3/40* (2024.01)
*G06T 5/70* (2024.01)
*G06T 5/73* (2024.01)
*G16H 30/20* (2018.01)

(52) U.S. Cl.

CPC ............... *G16H 30/40* (2018.01); *G06T 3/40* (2013.01); *G06T 5/70* (2024.01); *G06T 5/73* (2024.01); *G16H 30/20* (2018.01)

(58) Field of Classification Search

CPC .......... G16H 30/40; G16H 30/20; G06T 5/73; G06T 5/70; G06T 3/40

See application file for complete search history.

(56) References Cited

U.S. PATENT DOCUMENTS 11,599,977 B2 * 3/2023 Schreiber .................. G06T 5/20
2010/0142790 A1 * 6/2010 Chang ....................... G06T 5/70
382/274

(Continued)

OTHER PUBLICATIONS

NPL: IP.com and IEEE, Results Publication Date Range: Nov. 14, 1995 to Dec. 11, 2025.*

(Continued)

*Primary Examiner* — Quang N Vo
(74) *Attorney, Agent, or Firm* — Lempia Summerfield Katz LLC

(57) ABSTRACT

A method for digital image processing of medical images of an examination object recorded with a medical imaging device is provided. The method includes providing a respective band-pass or low-pass image for calculating an associated gradient field for at least a first level and for a further level of frequency decomposition of the medical image. A dot product is determined from the gradient field of the band-pass or low-pass image of the first level and the gradient field of the band-pass or low-pass image of the further level, which is adapted with respect to the image resolution of the band-pass or low-pass image. A mask image is ascertained for the first level by normalizing the dot product, and the ascertained mask image is integrated for the first level into a parameterization for processing the band-pass or low-pass image of the first level. An image processing operation is performed with the mask image integrated into the parameterization.

16 Claims, 4 Drawing Sheets

(56) References Cited

U.S. PATENT DOCUMENTS

2013/0148871 A1 6/2013 Kwon
2021/0249139 A1* 8/2021 Thakore ............... G06V 30/424

OTHER PUBLICATIONS

NPL: InnovationQ+ by IP.com and IEEE: Results Publication Date Range: Jan. 9, 1997 to Dec. 16, 2025.*
A. Frangi et al., "Multiscale Vessel Enhancement Filtering," In: MICCAI, pp. 130-137, Springer-Verlag, 1998, pp. 1-8.
Burt, P. J., et al., "The Laplacian Pyramid as a Compact Image Code", IEEE Transactions on Communications, vol. Com-31, No. 4, Apr. 1983, pp. 532-540.
Cho C. et al., "Effective Five Directional Partial Derivatives-Based Image Smoothing and a Parallel Structure Design," in IEEE Transactions on Image Processing, vol. 25, No. 4, 2016, pp. 1617-1625.
Gambaruto A. M.: "Processing the image 1-13 gradient field using a topographic primal sketch approach"; International Journal for Numerical Methods in Biomedical Engineering, John Wiley & Sons, Inc, Hoboken, USA, Bd. 31, Nr. 3; Feb. 13, 2015, pp. 1-24.
Stahl M. et al: "Digital Radiography Enhancement by Nonlinear Multiscale Processing II"; Medical Physics; AIP; Melville, NY, US, Bd. 27, Nr. 1, Jan. 1, 2000 (Jan. 1, 2000); pp. 56-65.
Tomasi, Carlo et al.: "Bilateral Filtering for Gray and Color Images"; 6th IEEE International Conference on Computer Vision; ICCV 1998; Bombay; India; Jan. 7, 1998; Conference Proceedings; ISBN 81-7319-221-9; (1998), pp. 839-846.

* cited by examiner

Provision of recorded medical image
20
Gaussian-Laplacian frequency decomposition in a plurality of levels
21
Provision of band-pass images and calculation of gradient fields for first and further level
22
Determination of dot product
23
Ascertaining mask image
24
Integration of mask image into parameterization
25
Image processing
26

METHOD FOR DIGITAL IMAGE PROCESSING OF MEDICAL IMAGES RECORDED WITH A MEDICAL IMAGING DEVICE AND COMPLETE MEDICAL SYSTEM

This application claims the benefit of European Patent Application No. EP 22215016.1, filed on Dec. 20, 2022, which is hereby incorporated by reference in its entirety.

BACKGROUND

The present embodiments relate to digital image processing of medical images of an examination object recorded with a medical imaging device.

In the context of medical imaging and, for example, X-ray imaging (e.g., interventional X-ray imaging, fluoroscopy, angiography, or radiography), image quality plays a major role in establishing a diagnosis. The (subjective) image quality of medical images of an examination object recorded by an imaging system depends largely on the definition (e.g., edge definition) of relevant structures and on the optical separability of the relevant structures against an image background. Both the edge definition and separability of the relevant structures are negatively affected by noise, where a low dose (e.g., X-ray dose) further aggravates this. A clear artifact-free demarcation of relevant structures from the background of the image is therefore an important goal.

In the simplest case, the definition or highlighting of structures or contours in the medical image is achieved by boosting higher image frequencies (e.g., ≙ high-pass image), but this homogeneously amplifies all corresponding frequency components (e.g., including noise) in the image. In addition, this approach is accompanied by mostly undesirable effects, such as the halo effect (e.g., bright overexposed borders) on the highlighted edges. One possible procedure for reducing the increase in noise is weighting or parametrization by a gradient field (e.g., edge amplification that is dependent on the gradient field). Other possible methods for edge definition include edge-preserving smoothing and bilateral filters (e.g., C. Cho and S. Lee, "Effective Five Directional Partial Derivatives-Based Image Smoothing and a Parallel Structure Design," in IEEE Transactions on Image Processing, vol. 25, no. 4, 2016, pp. 1617-1625, or C. Tomasi and R. Manduchi, "Bilateral filtering for gray and color images," Sixth International Conference on Computer Vision, Bombay, 1998, pp. 839-846), but these mainly minimize artifact-generating directions of action and do not improve the actual contour definition.

Another possibility is to reduce the visual relevance of the background of the image. Frequency filters or gray value mapping may be used for this purpose, for example. However, frequency filters have a homogeneous effect on the entire frequency range and generate halo effects. Gray value mapping is only suitable to a limited extent because assumptions are made about the gray value ranges of image content. Advanced approaches are based on segmentation, where assumptions regarding the content to be separated are a prerequisite, for example "tubular structure" (e.g., enhancing vessel-like structures using Frangi vesselness filters, see, for example, Frangi et al., "Multiscale vessel enhancement filtering," in: Medical Image Computing and Computer-Assisted Intervention—MICCAI'98, W. M. Wells, A. Colchester and S. L. Delp (Eds.), Lecture Notes in Computer Science, vol. 1496, Springer Verlag, Berlin, Germany, 1998, pp. 130-137).

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for digital image processing for medical images (e.g., X-ray images) that overcomes the problems of the prior art and enables sharper edge definition without noise amplification and without artifacts is provided. As another example, a complete medical system suitable for performing the method is provided.

According to the present embodiments, a method for digital image processing of medical images of an examination object recorded with a medical imaging device is provided. A recorded medical image is decomposed into a plurality of levels by frequency decomposition according to Gaussian-Laplacian decomposition. A complete medical system is also provided.

The method according to the present embodiments for digital image processing of medical images of an examination object recorded with a medical imaging device is provided. A recorded medical image is decomposed into a plurality of levels by frequency decomposition according to Gaussian-Laplacian decomposition. The method includes: a) providing a respective band-pass or low-pass image for calculating an associated gradient field for at least a first level and for a further level of frequency decomposition of the medical image; b) determining a dot product from the gradient field of the band-pass or low-pass image of the first level and the gradient field of the band-pass or low-pass image of the further level, which is, for example, adapted with respect to the image resolution of the band-pass or low-pass image; c) ascertaining a mask image for the first level by normalizing the dot product; d) integrating the ascertained mask image for the first level into a parameterization for processing the band-pass or low-pass image of the first level; and e) performing an image processing operation with the mask image integrated into the parameterization.

The idea behind the method is based on the recognition that relevant image content of a medical image is distributed between a plurality of (e.g., adjacent) frequency decomposition levels, whereas noise is not manifested consistently across levels. With this recognition, in the context of the method, a mask image is determined for at least one level of frequency decomposition, which uses a combination of two gradient fields of band-pass or low-pass filters of different levels. In principle, a gradient field is a field of vectors (e.g., two-dimensional vectors in the case of medical images). During frequency decomposition of an image, these vectors are aligned across adjacent levels in the case of relevant structures and, in contrast, are randomly distributed in the case of noise.

Incorporating the mask image determined in this way into the parameterization when processing the associated level enables simultaneously sharper and artifact-reduced edge definition to be achieved. One reason for this is that the mask image identifies and selects precisely the edge regions for which such edge definition is possible. The method makes it easier to identify relevant structures against the image background, and artifacts such as halo effects are avoided. There is no need for a prior assumption of expected structures to be fed into the image processing in order to achieve good results. In addition, regions of the medical image without contours may be smoothed. Overall, the image quality of medical images is significantly improved, and this leads to improved diagnosis and better therapeutic outcomes, and thus to better patient care.

The principle of Gaussian-Laplacian frequency decomposition of an image is known, see for example P. J. Burt, E. H. Adelson, "The Laplacian Pyramid as a Compact Image Code," 1983, IEEE Transactions on Communications, vol. com-31, no. 4. In order to obtain a Gaussian-Laplacian pyramid, first, a Gaussian pyramid may be ascertained. This may be described as follows: the original medical image is the lowest level of the pyramid, and the next level is calculated via low-pass convolution (e.g., convolution with a Gaussian bell) and bisecting (e.g., not mandatory, may also be omitted) the support points. This is repeated until the topmost image reaches a size of 1×1 pixels. It is then possible to ascertain a Laplacian pyramid from the Gaussian pyramid by determining a Laplacian level from the difference between two adjacent Gaussian levels. The Gaussian levels and Laplacian levels may often also be ascertained in parallel. To provide that the frequency images of adjacent Gaussian levels are of the same size, interpolation is applied to the higher level (e.g., with lower resolution). The individual Laplacian levels of the Laplacian pyramid represent the image content in the spatial frequency range assigned to the respective level (e.g., band-pass images).

The mask image is determined by suitably normalizing the pixel values of the respective dot product to the interval [0,1].

In the context of the method, the first level may not generally be understood to be the first level according to the order of frequency decomposition, but only any selected level for which the method is performed. However, it may be useful, for example, if only one mask image is ascertained and used for the entire medical image, to use the lowest (e.g., "first") level according to the order of frequency decomposition as the first level.

Following the image processing described in the method, the processed levels are usually recombined according to their decomposition in order to obtain a result image.

According to one embodiment, the further level is formed by a level adjacent to the first level (e.g., an adjacent level with lower image resolution; generally, the level lying above according to the pyramid). Therefore, if, for example, the first level is the lowest level $E_1$, the second-lowest level $E_2$ above this is used as the further level, for example. The use of adjacent levels for this purpose in the context of the method provides that relevant structures are defined more sharply since these are consistently identifiable (e.g., in the case of adjacent levels), and that noise is not amplified since there is no such consistency for noise.

According to a further embodiment, acts a to d are performed for at least two different levels, and act e is performed with at least two mask images integrated into the respective parameterization. The more mask images there are, the more sharply the edges may be defined, and the better the image quality is likely to be. For example, acts a to d are performed for a plurality of levels or even all levels apart from the uppermost level of frequency decomposition, and act e is performed with the plurality of integrated mask images. This results in an optimally sharpened structure and thus optimal image quality of the medical image.

According to a further embodiment, a band-pass image $v_L$ is determined for the first level (e.g., as the first selected level) of frequency decomposition using the following formula:

$$v_L := (\mathbb{1}_L - I_L T_{L+1}^L R_L^{L+1} S_L) \cdot u_L,$$

where L is the numbering of the first level with respect to the order of frequency decomposition, $$R_L^{L+1}$$

is a resolution-downsampling operator, $$T_{L+1}^L$$

is a resolution-upsampling operator, S is a smoothing operator, I is an interpolation operator, $\mathbb{1}_L$ is an identity operator, and $u_L$ is the respective input image of the first level. The formula is a common representation for determining a band-pass image of a level of the Laplacian pyramid.

According to a further embodiment, the gradient field of the band-pass or low-pass image of the further level (e.g., the level adjacent to the first level) is adapted with respect to the image resolution of the band-pass or low-pass image (e.g., using a resolution-upsampling operator $$(T_{L+1}^L)).$$

This is useful in order to be able to determine the dot product in a simple manner.

According to a further embodiment, the dot product is formed by the formula $$\langle \nabla v_L, I_L T_{L+1}^L \nabla v_{L+1} \rangle \text{ or by the formula } \langle \nabla v_L, I_L T_{L+1}^L \nabla u_{L+1} \rangle,$$

where $\nabla v_L$ is the gradient field of the band-pass image of the first level, $\nabla v_{L+1}$ is the gradient field of the band-pass image of the further level, $$T_{L+1}^L$$

is a resolution-upsampling operator, $I_L$ is an interpolation operator, and $\nabla u_{L+1}$ is the gradient field of the respective input image of the further level. This is a usual representation for a dot product, where the image resolution of the adjacent band-pass image (e.g., with the lower resolution) is adapted to the higher resolution in order to enable rapid and easy determination.

According to a further embodiment, the mask image $\Theta_L$ is determined from the dot product using the following formula:

$$\Theta_L := \overline{\langle \nabla v_L, I_L T_{L+1}^L \nabla v_{L+1} \rangle},$$

where $\nabla v_L$ is the gradient field of the band-pass image of the first level, $\nabla v_{L+1}$ is the gradient field of the band-pass image of the further level, $$T_{L+1}^{L}$$

is a resolution-upsampling operator, and $I_L$ is an interpolation operator. Thus, the mask image results from normalization of the dot product so that its value range is [0,1]. High values close to 1 mark the edges of relevant structures relative to the band-pass image $v_L$, and no relevant structures may be found at low values.

In one embodiment, the corresponding mask image is configured to effect a sharper definition of contours of edges or relevant structures present in the medical image (e.g., an object such as an organ, bone, or blood vessel). Relevant structures are present at a number of levels of frequency decomposition, and hence, high values close to 1 may be found for the mask image at the positions of the relevant structures. Corresponding image processing in the region of the structures effects a sharper definition of the edges. In one embodiment, the mask image is configured to effect smoothing of regions of the medical image without contours or with poorly pronounced contours, which is achieved at these positions by the low values of the mask image close to 0.

According to a further embodiment, at least one pre-trained machine-learning algorithm is used to perform the method. This may be particularly suitable for achieving a rapid and simple performance of the method.

The present embodiments also include a complete medical system for digital image processing of medical images of an examination object recorded by a medical imaging device according to the method, which has a provisioning unit for providing at least one medical image, an image processing unit for processing and frequency decomposition of medical images (e.g., using at least one image processing algorithm), a control unit for actuating the complete medical system, and an output unit for outputting the processed medical image. The image processing unit is, for example, configured to: determine a band-pass or low-pass image and an associated gradient field for at least a first level and for a further level of frequency decomposition of the medical image; determine a dot product from the gradient field of the band-pass or low-pass image of the first level and the gradient field of the band-pass or low-pass image of the further level; ascertain a mask image for the first level by normalizing the dot product; integrate this into a parameterization of the band-pass or high-pass image of the first level; and perform an image processing operation in this way. For example, one or more algorithms are configured to execute the acts of the method.

The present embodiments also include a computer program product with at least one algorithm for digital image processing for performing the method.

BRIEF DESCRIPTION OF THE DRAWINGS

The invention and further embodiments are explained in more detail below with reference to schematically illustrated embodiments in the drawing without thereby restricting the invention to these embodiments. The drawings show.

DETAILED DESCRIPTION

Figure 1:
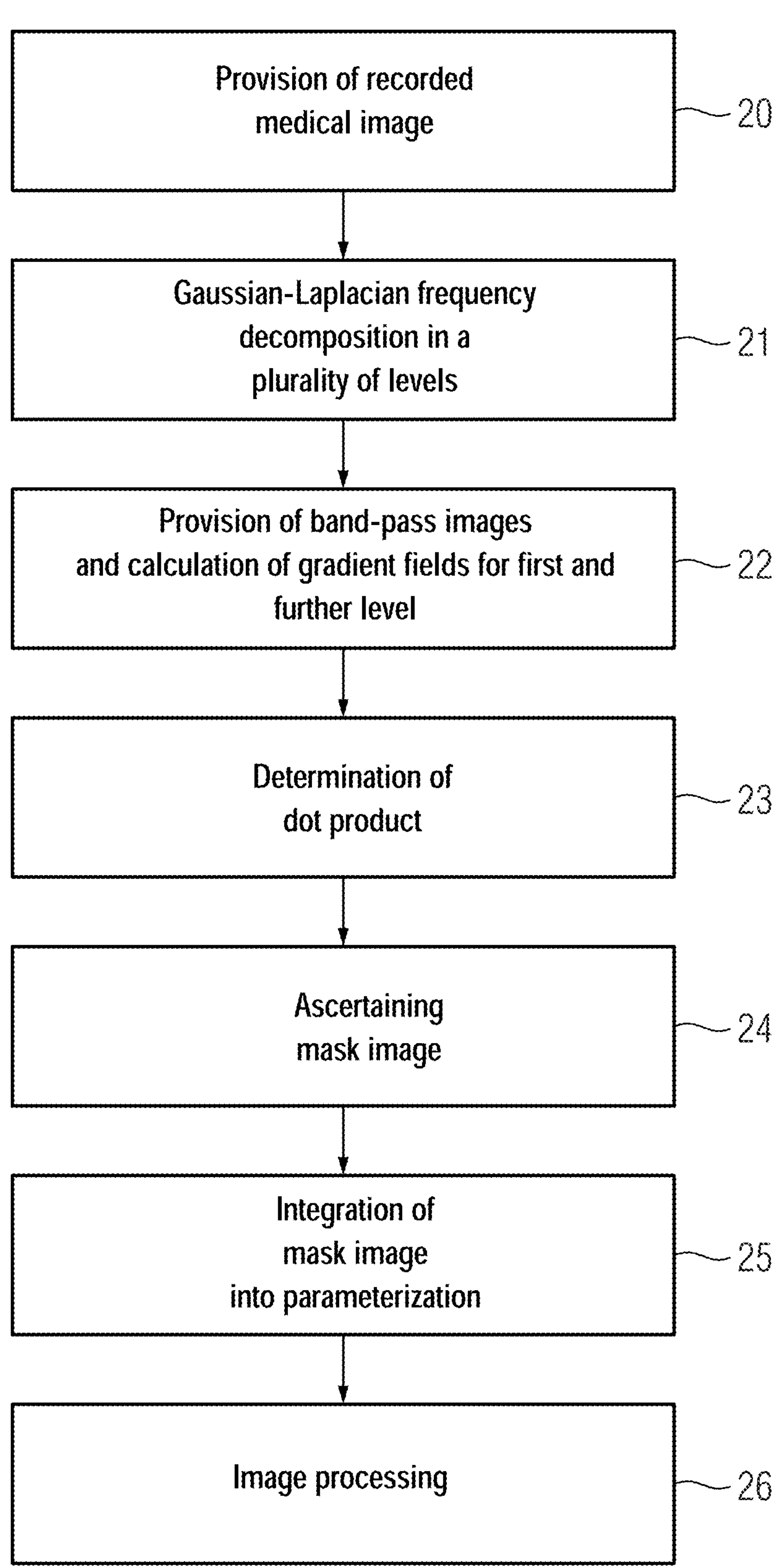
FIG. 1 shows a sequence of acts of a method according to the present embodiments.
Figure 8:
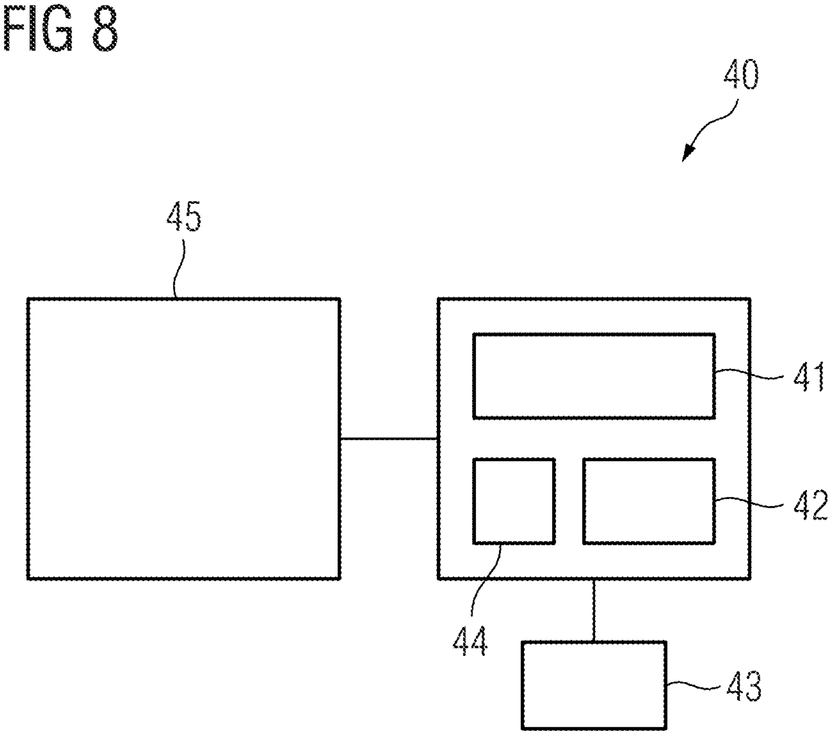
FIG. 8 is a view of an example of a complete medical system.

FIG. 1 shows acts of a method for digital image processing of medical images of an examination object recorded with a medical imaging device. The medical images may, for example, be recorded by an X-ray device (e.g., two-dimensional (2D) projection images). FIG. 8 shows a complete system 40 for performing the method. The method makes it possible to define relevant structures, such as organs or other objects, more sharply without artifacts and to reduce or smooth noise, and in this way, to achieve high image quality. High image quality is particularly necessary for medical images or X-ray images in order to be able to establish a good diagnosis. In the case of fluoroscopy monitoring during an interventional procedure, it is important to apply as low a dose as possible by permanent X-ray radiation, and this may also lead to high noise.

The approach described here is based on frequency decomposition of the medical image in a Laplacian pyramid and the comparatively open assumption that relevant image content is distributed between a plurality of (e.g., adjacent) levels (e.g., band-pass or deep-pass images) of this decomposition, whereas noise is not consistently manifested across levels.

In a first act 20, a medical image (e.g., a (2D) X-ray image) is provided. Herein, the medical image may either be taken from a memory or a database or even recorded directly using an imaging device assigned to the complete system 40 (e.g., angiography X-ray device, permanently installed or mobile C-arm X-ray device, CT, or the like) and, for example, provided by a provisioning unit 41. The medical image was created by X-ray fluoroscopy of an examination object (e.g., a patient's organ or body part). This may, for example, entail a patient's heart, blood vessel, liver, lung, spinal column, or bone. The medical image may be still unprocessed or already partially processed. Medical images are generally post-processed after recording using a range of image-processing methods, for example, to improve image quality and correct movement, artifacts, or noise effects.

In a second act 21, the medical image is decomposed into a plurality of levels using Gaussian-Laplacian frequency decomposition. Such frequency decomposition is known from the prior art and may be performed as standard. The order may, for example, be such that first Gaussian-decomposition is performed, and then, Laplacian decomposition is performed. This may be performed both in principle (e.g., first, the entire Gaussian-decomposition, and then, the Laplacian decomposition) and for individual levels (e.g., first the Gaussian level, and then, the corresponding Laplacian level). Frequently, both decompositions are performed in parallel (e.g., level by level). The results of the Gaussian-decomposition (e.g., deep-pass images) may be retained if required or discarded if the results are not needed. An image processing unit 42 may be used to perform the Gaussian-Laplacian frequency decomposition.

In a third act 22, a respective band-pass image calculated in accordance with the previously performed decomposition is provided for a first level and for a further level of frequency decomposition, and an associated gradient field is calculated therefrom. Here, designation as the first level is not intended to refer to the order of frequency decomposition (e.g., not to the "lowest" level of frequency decomposition, but rather, to stand generally for the respective level selected for the method). Therefore, in the following, the index L is used, and the adjacent further level is numbered L+1. Therefore, for Laplacian frequency decomposition into N levels $E_i$ ($i \in [1 \ldots N]$), the index L may stand for one level $E_L$ of the levels $E_1$ to $E_{N-1}$.

In Laplacian frequency decomposition, $v_L$ is intended to be the band-pass image at the first level, and $u_L$ is the associated input image (e.g., of the Gaussian pyramid), so that $$v_L := \left(\mathbb{1}_L - I_L T_{L+1}^L R_L^{L+1} S_L\right) \cdot u_L.$$

T and R are operators for resolution upsampling (T) or resolution downsampling (R) between levels L and L+1, and I and S are suitable convolution operators for interpolation (I) and smoothing (S). For example, $u_1$ is the unprocessed input image (e.g., the originally recorded medical image) before decomposition. $\mathbb{1}$ is an identity operator. The corresponding gradient fields are $\nabla v_L$ and $\nabla V_{L+1}$. The third act 22 may likewise be performed by the image processing unit 42 or a further computing unit. One or more algorithms may be used for this. The second act 21 and the third act 22 may also be performed together.

In a fourth act 23, starting from the gradient fields $\nabla v_L$ and $\nabla V_{L+1}$, the dot product $$\langle \nabla v_L, I_L T_{L+1}^L \nabla v_{L+1} \rangle$$

is calculated from the gradient fields of the first level and its adjacent level. Here, the operators I (e.g., interpolation) and T (e.g., resolution upsampling) act on the gradient field of the further level component by component. Resolution upsampling increases the resolution of the gradient field of the L+1-th level to the L-th level. Depending on the design of the pyramid and the level index L, it may be advantageous to use $$\langle \nabla v_L, I_L T_{L+1}^L \nabla u_{L+1} \rangle.$$

However, we will restrict ourselves to the first variant for the further description. The calculation of the dot product may, for example, be performed by the image processing unit 42 or another computing unit.

Figure 2:
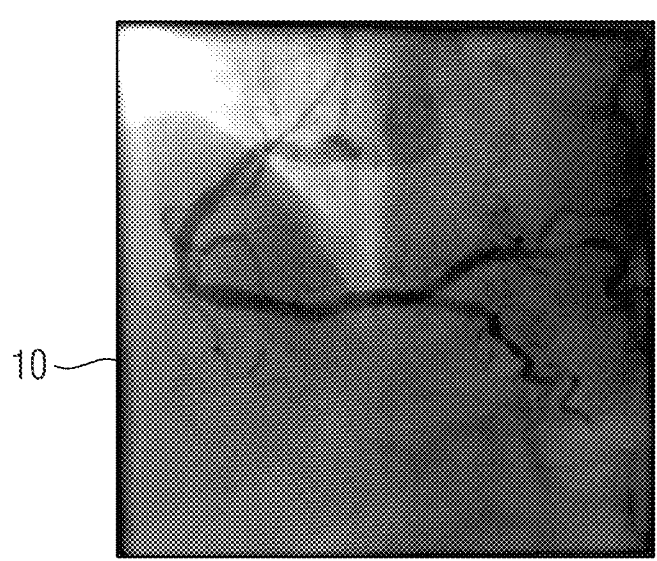
FIG. 2 is a view of an example of a medical image.
Figure 3:
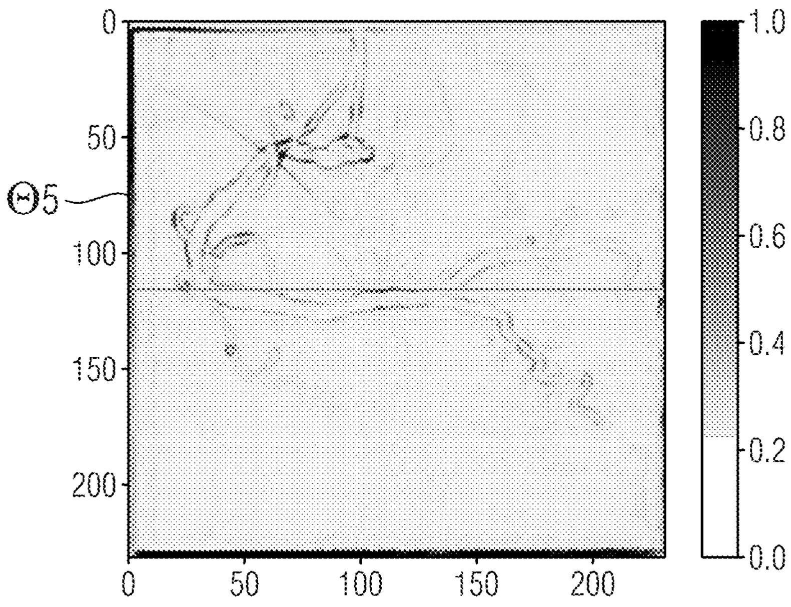
FIG. 3 is a view of an example of a mask image determined from a frequency decomposition of the medical image in FIG. 2.

In a fifth act 24, a mask image $$\Theta_L := \overline{\langle \nabla v_L, I_L T_{L+1}^L \nabla v_{L+1} \rangle}$$

for the first level (e.g., index L) is then calculated from the dot product calculated in the fourth act 23 by suitable normalization. The mask image has a value range [0,1]. Higher values over 0.5, for example, mark relevant structures or objects and their edges in relation to the band-pass image $v_L$. Low values in the range of 0 do not contain any relevant structures, but may, for example, contain noise. FIGS. 2 and 3 show an example of a medical image 10 of a vascular tree (see FIG. 2) and a mask image $\Theta_5$ (see Figure) of the fifth-lowest Laplacian level (by way of example only) ascertained for this purpose. The structures of the vessel edges may be clearly identified, and the background has a value range close to 0.

Then, in a sixth act 25, the mask image $\Theta_L$ is integrated into the parameterization of the processing of the first band-pass image $v_L$. This provides that the mask image is included in the processing of the band-pass image $v_L$ as a parameter or amplification factor. In the present case, the effect of the mask image is that the pixels of the band-pass image $v_L$ are amplified in the regions of the mask image with high values compared to those with low values (see also FIG. 7, explanation below).

The mask image installed in this way is then used for an image processing operation in a seventh act 26. This may also contain further parameters (e.g., noise reduction, smoothing, artifact reduction, correction, etc.). In the course of the image processing operation, the mask image is, for example, used to define the contours more sharply without creating artifacts such as halos or smoothing the edges. In this way, it is also possible for contour-free regions to be smoothed, which significantly reduces noise without blurring edges.

The image processing described in the method is usually followed by the recombination of the processed levels according to their decomposition in order to obtain a result image.

Figure 4:
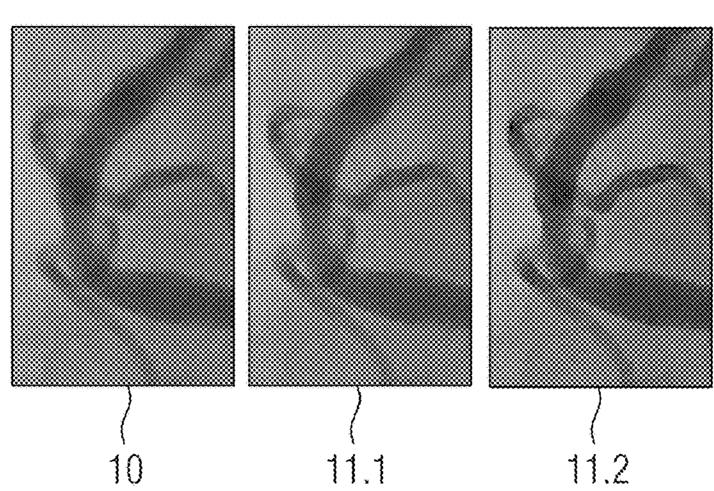
FIG. 4 is a view of an example of an originally unprocessed medical image and examples of two images resulting after using the method.

FIG. 4 shows a medical image 10 of a further vascular tree and two medical images 11.1 and 11.2 processed by the method. The images 11.1 and 11.2 processed according to the method show the improvement in image quality due to the enhanced edge definition in two examples of parameterization. Herein, a slightly enhanced edge definition may be identified in the middle image 11.1, and a very strong edge definition may be identified in the right image 11.2.

The third act 22, the fourth act 23, the fifth act 24, and the sixth act 25 may also be repeated for a second level (e.g., index M, also possible from 1 to N−1, where L≠M; adjacent level M+1) if required, so that a further mask image $\Theta_M$ is then ascertained for the second level. The seventh act 26 (e.g., image processing) is then performed with mask images $\Theta_L$ and $\Theta_M$ integrated into the parameterization of the band-pass images $v_L$ and $v_M$ of their respective levels (e.g., indices L and M).

The third act 22, the fourth act 23, the fifth act 24, and the sixth act 25 may optionally also be performed for a plurality of levels or all levels (e.g., apart from the uppermost level since this has no further adjacent levels). The mask images obtained in this way may then be integrated into the parameterization of the band-pass images of their respective levels, and image processing may be performed with the integrated mask images.

In some cases, instead of the further level adjacent to the first level, it is also possible to use a non-adjacent further level (e.g., the next-but-one adjacent level (L+2)). However, a level with the same or lower resolution may always be used, not a level with higher resolution. In principle, pairs of levels $E_i$ and $E_{i+d}$ where d>0 may be used.

Figure 5:
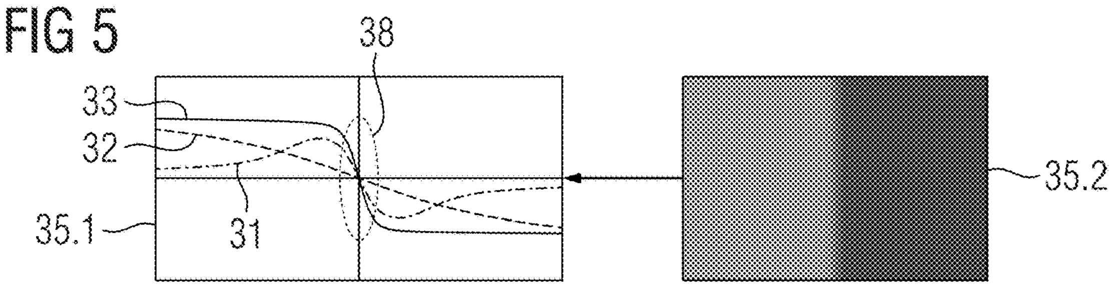
FIG. 5 is a view of an example of a typical edge in a medical image and an example of an associated frequency decomposition reduced to high-pass and low-pass.

In order to illustrate the mode of operation of the method with respect to the improved edge definition, FIG. 5 shows a common blurred structure edge in a first frequency decomposition 35.1 reduced to the minimum of a high-pass and a deep-pass and their approximately corresponding first gray value representation 35.2. The first frequency decomposition 35.1 shows the high-pass curve 31 and the deep-pass curve 32 along the horizontal line of intersection 33 through the structure edge. A visually sharp definition of the edge depends on the steepness of the line of intersection 33 in the edge region 38 marked with dashed lines. Edge-preserving smoothing has no effect on this image, since the structure edge is already perfectly smooth along its vertical alignment.

Figure 6:
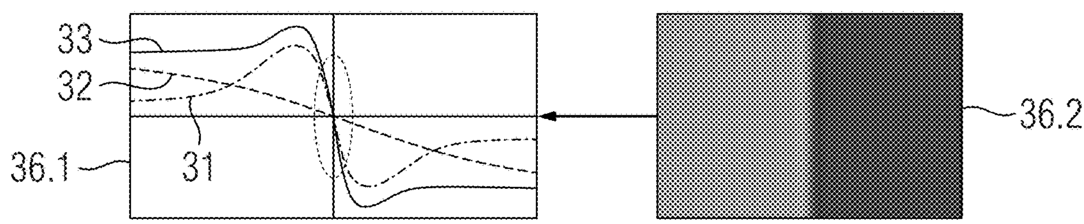
FIG. 6 is a view of the edge in FIG. 5, which has been amplified by edge enhancement according to the prior art.

In FIG. 6, the second frequency decomposition 36.1 shows the result of a known edge enhancement method, which significantly enhances the high-pass curve 31 and increases the steepness of the line of intersection 33 near to the center of the edge. However, this results in an undesirable halo effect that may be identified in the second gray value representation 36.2.

Figure 7:
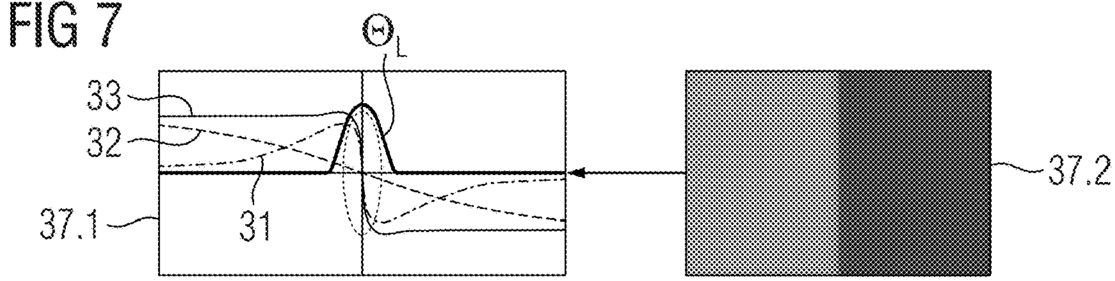
FIG. 7 is a view of the edge in FIG. 5 sharpened according to the method and an example of an associated mask image.

FIG. 7 shows the result of the described method in a third frequency decomposition 37.1, where at the same time, it is possible to see the value range of the mask image Q along the edge. Overall, amplification of the high-pass curve 31 was restricted to the region relevant for the sharp definition of the edge. This enabled the width of the transition between the two gray values of the third gray value representation 37.2 to be reduced and the usual artifacts, such as halos, to be kept to a minimum.

Depending upon the interpretation of Q, the method described may be used variably to smooth and/or define the edge definition of the medical image. Herein, edges are not amplified or smoothed to preserve edges as in conventional methods; instead, the contours are defined more sharply. Using a combination of two gradient fields of band-pass and/or deep-pass filters of different frequency ranges not only enables contours of relevant objects to be detected, but, for example, also enables the identification of precisely those edge regions within the higher-frequency band-pass image that may be modified for sharper, but artifact-reduced, edge definition.

FIG. 8 shows the complete medical system 40 for performing the method. This includes a provisioning unit 44 for providing at least one medical image, an image processing unit 42 for processing and frequency decomposition of medical images (e.g., using at least one image processing algorithm), a control unit 41 for actuating the complete medical system, and a display unit 43 for outputting the processed medical image. An X-ray device 45 is assigned to the complete system 40.

Regardless of the grammatical gender of a specific term, individuals who identify as male, female, or another gender are also included.

The present embodiments may be briefly summarized as follows. The method according to the present embodiments for digital image processing of medical images of an examination object recorded with a medical imaging device, where a recorded medical image is decomposed into a plurality of levels using frequency decomposition according to Gaussian-Laplacian decomposition, includes the following acts: a) providing a respective band-pass or low-pass image for calculating an associated gradient field for at least a first level and for a further level of frequency decomposition of the medical image; b) determining a dot product from the gradient field of the band-pass or low-pass image of the first level and the gradient field of the band-pass or low-pass image of the further level, which is, for example, adapted with respect to the image resolution of the band-pass or low-pass image; c) ascertaining a mask image for the first level by normalizing the dot product; d) integrating the ascertained mask image for the first level into a parameterization for processing the band-pass or high-pass image of the first level; and e) performing an image processing operation with the mask image integrated into the parameterization.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for digital image processing of medical images of an examination object recorded with a medical imaging device, wherein a recorded medical image is decomposed into a plurality of levels using frequency decomposition according to Gaussian-Laplacian decomposition, the method comprising:

providing a respective band-pass or low-pass image for calculating an associated gradient field for at least a first level and for a further level of frequency decomposition of the recorded medical image;

determining a dot product from the gradient field of the band-pass or low-pass image of the first level and the gradient field of the band-pass or low-pass image of the further level, which is adapted with respect to an image resolution of the band-pass or low-pass image;

ascertaining a mask image for the first level, the ascertaining of the mask image comprising normalizing the dot product;

integrating the ascertained mask image for the first level into a parameterization for processing the band-pass or low-pass image of the first level; and performing an image processing operation with the mask image integrated into the parameterization.

2. The method of claim 1, wherein the further level is formed by a level adjacent to the first level.

3. The method of claim 2, wherein the level adjacent to the first level is an adjacent level with lower image resolution.

4. The method of claim 1, wherein the providing, the determining, the ascertaining, and the integrating are performed for at least two different levels, and the performing is performed with at least two integrated mask images.

5. The method of claim 1, wherein the providing, the determining, the ascertaining, and the integrating are performed for a plurality of levels of frequency decomposition, and the performing is performed with the plurality of integrated mask images.

6. The method of claim 1, wherein a band-pass image for the first level is determined using the following formula:

$$v_L := (\mathbb{1}_L - I_L T_{L+1}^L R_L^{L+1} S_L) \cdot u_L,$$

and wherein L is a numbering of the first level, $$R_L^{L+1}$$

is a resolution-downsampling operator, $$T_{L+1}^L$$

is a resolution-upsampling operator, S is a smoothing operator, I is an interpolation operator, $\mathbb{1}_L$ is an identity operator, and $u_L$ is a respective input image of the first level.

7. The method of claim 1, wherein the gradient field of the band-pass or low-pass image of the further level is adapted with respect to the image resolution of the band-pass or low-pass image.

8. The method of claim 7, wherein the gradient field of the band-pass or low-pass image of the level adjacent to the first level is adapted with respect to the image resolution of the band-pass or low-pass image using a resolution-upsampling operator.

9. The method of claim 1, wherein the dot product is formed by the formula:

$$\langle \nabla v_L, I_L T_{L+1}^L \nabla v_{L+1} \rangle \text{ or } \langle \nabla v_L, I_L T_{L+1}^L \nabla u_{L+1} \rangle,$$

and wherein $\nabla v_L$ is the gradient field of the band-pass image of the first level, $\nabla v_{L+1}$ is the gradient field of the band-pass image of the further level, $$T_{L+1}^L$$

is a resolution-upsampling operator, $I_L$ is an interpolation operator, and $\nabla u_{L+1}$ is the gradient field of the respective input image of the further level.

10. The method of claim 1, wherein ascertaining the mask image comprises determining the mask image from the dot product using the following formula:

$$\Theta_L := \overline{\langle \nabla v_L, I_L T_{L+1}^L \nabla v_{L+1} \rangle},$$

and wherein $\nabla v_L$ is the gradient field of the band-pass image of the first level, $\nabla v_{L+1}$ is the gradient field of the band-pass image of the further level, $$T_{L+1}^L$$

is a resolution-upsampling operator, and $I_L$ is an interpolation operator.

11. The method of claim 1, wherein the mask image is configured to effect a sharper definition of contours of edges present in the medical image.

12. The method of claim 1, wherein the mask image is configured to effect smoothing of regions of the medical image without contours or with poorly pronounced contours.

13. The method of claim 1, wherein at least one machine-learning algorithm is used to perform the method.

14. A complete medical system for digital image processing of medical images of an examination object recorded by an imaging device, the complete medical system comprising:

- a provisioning unit configured to provide at least one medical image;
- an image processing unit configured for processing and frequency decomposition of medical images;
- a control unit configured to actuate the complete medical system; and
- an output unit configured to output the processed medical image,
- wherein the complete medical system is configured for digital image processing of medical images of an examination object recorded with a medical imaging device, wherein a recorded medical image is decomposed into a plurality of levels using frequency decomposition according to Gaussian-Laplacian decomposition, the complete medical system being configured for digital image processing of medical images comprising the complete medical system being configured to:
- provide a respective band-pass or low-pass image for calculating an associated gradient field for at least a first level and for a further level of frequency decomposition of the recorded medical image;
- determine a dot product from the gradient field of the band-pass or low-pass image of the first level and the gradient field of the band-pass or low-pass image of the further level, which is adapted with respect to an image resolution of the band-pass or low-pass image;
- ascertain a mask image for the first level, the ascertainment of the mask image comprising normalization of the dot product;
- integrate the ascertained mask image for the first level into a parameterization for processing the band-pass or low-pass image of the first level; and
- perform an image processing operation with the mask image integrated into the parameterization.

15. The complete medical system of claim 14, wherein the image processing unit is configured for processing and frequency decomposition of the medical images using at least one image processing algorithm.

16. In a non-transitory computer-readable storage medium that stores instructions executable by one or more processors for digital image processing of medical images of an examination object recorded with a medical imaging device, wherein a recorded medical image is decomposed into a plurality of levels using frequency decomposition according to Gaussian-Laplacian decomposition, the instructions comprising:

- providing a respective band-pass or low-pass image for calculating an associated gradient field for at least a first level and for a further level of frequency decomposition of the recorded medical image;
- determining a dot product from the gradient field of the band-pass or low-pass image of the first level and the gradient field of the band-pass or low-pass image of the further level, which is adapted with respect to an image resolution of the band-pass or low-pass image;

ascertaining a mask image for the first level, the ascertaining of the mask image comprising normalizing the dot product;

integrating the ascertained mask image for the first level into a parameterization for processing the band-pass or low-pass image of the first level; and performing an image processing operation with the mask image integrated into the parameterization.

* * * * *